United States Patent [19]
Ramana et al.

[11] Patent Number: 5,491,094
[45] Date of Patent: Feb. 13, 1996

[54] TEST STRIP FOR FREE CHLORINE ANALYSIS

[75] Inventors: Vasili V. Ramana; Kami R. Yamuna; Ivars Jaunakais, all of Rock Hill, S.C.

[73] Assignee: Industrial Test Systems, Inc., Rock Hill, S.C.

[21] Appl. No.: 253,959

[22] Filed: Jun. 3, 1994

[51] Int. Cl.⁶ .................................... G01N 33/00
[52] U.S. Cl. .................. 436/125; 436/169; 436/810; 436/904; 435/4; 435/14; 435/805; 427/2.13; 422/56
[58] Field of Search ................... 422/55–58, 86, 422/87; 436/124, 125, 169, 810, 904; 435/4, 14, 291, 805; 427/2.13

[56] References Cited

U.S. PATENT DOCUMENTS

| | | | |
|---|---|---|---|
| 1,986,403 | 1/1935 | Lehmkuhl | 422/61 |
| 3,453,180 | 7/1969 | Fraser, Jr. et al. | 195/99 |
| 3,510,263 | 5/1970 | Hach | 422/56 |
| 4,092,115 | 5/1978 | Rupe et al. | 23/230 R |
| 4,273,868 | 6/1981 | Walter | 435/14 |
| 4,275,031 | 6/1981 | Fischer et al. | 422/57 |
| 4,339,243 | 7/1982 | Magers et al. | 436/154 |
| 4,385,114 | 5/1983 | Guthlein et al. | 435/28 |
| 4,390,621 | 6/1983 | Bauer | 435/14 |
| 5,187,100 | 2/1993 | Matzinger et al. | 436/16 |

FOREIGN PATENT DOCUMENTS

| 818344 | 7/1969 | Canada | 31/132 |
|---|---|---|---|

OTHER PUBLICATIONS

Standard Methods for the Examination of Water and Wastewater, 18th Ed. 1992, pp. 4–36, 4–37, 4–47.
Ultra+ Blood Glucose Monitoring Test Strips, Directions for Use, Apr. 1992.

*Primary Examiner*—David A. Redding
*Attorney, Agent, or Firm*—Timothy R. Kroboth

[57] ABSTRACT

A colorimetric test strip useful for analysis of free chlorine is provided. In a preferred embodiment, 3,3',5,5'-tetramethylbenzidine is the colorimetric indicator. Beneficially, the carrier for the indicator has been treated to have a pH that eliminates chloramine interference. Advantageously, the indicator in free base form and a suitable water-soluble buffer may be deposited on the carrier using a combined solution of indicator and buffer.

20 Claims, 1 Drawing Sheet

TEST STRIP FOR FREE CHLORINE ANALYSIS

FIELD OF THE INVENTION

This invention relates to colorimetric test or reagent strips for detection of free chlorine.

BACKGROUND OF THE INVENTION

The use of free available chlorine as a disinfectant for swimming pool water and other water supplies, continues to be popular. Since the amount of free available chlorine in an aqueous solution relates directly to the disinfecting or sanitizing activity thereof, a test which rapidly and accurately measures free available chlorine has long been desired.

By comparison, chlorine associated with organic chloramines, is not believed to be effective for disinfecting. Accordingly, a test system that measures chloramines in addition to free available chlorine, is not truly indicative of the level of disinfectant.

Colorimetric tests for chlorine solutions using o-tolidine or an azine compound as a colorimetric indicator, are known. Illustrative are U.S. Pat. Nos. 1,986,403 to Lehmkuhl and 4,092,115 to Rupe. For determining free available chlorine, Rupe describes the use of an azine compound, a buffer system having a pH of from about 3.5 to 8.5, preferably about 6.0, and the use of phosphate buffer. A drawback is that the azine reagents do not produce a stable colored reaction product. Also known as exemplified by Canadian Patent No. 818,344 to Rupe, is a chloride test paper containing a diaminodiphenyl compound, preferably o-tolidine, and a cupric salt.

Also known as illustrated by U.S. Pat. No. 4,339,243 to Magers et al, is the stabilization of benzidine-type indicators with various enhancers. Evaluated therein is a test paper containing 3,3',5,5'-tetramethylbenzidine (TMB) for sodium hypochlorite solution, and prepared using pH 5 buffer. Various carrier matrices including a matrix of polyamide fibers, are disclosed.

As exemplified by U.S. Pat. Nos. 4,273,868 to Walter, 4,385,114 Guthlein et al and 4,390,621 to Bauer, also known is a test paper containing TMB for the detection of hydrogen peroxide, glucose, cholesterol and so forth. Coagents include a peroxide, oxidase or other enzymatic coagent. As illustrated in U.S. Pat. Nos. 4,273,868 and 4,385,114, multi-step impregnation by a free base formulation involves successive dips in a water-containing buffer solution, and an organic liquid-containing solution of TMB. As illustrated in the Walter patent, an interpolymer of methylvinyl ether and maleic anhydride may be used for color enhancement. As exemplified in the Bauer patent, a polyethoxylated fatty alcohol, nonionic surfactant may be used for color uniformity.

Test strips typically include an absorptive carrier bearing the colorimetric indicator, for instance, absorptive paper impregnated with the indicator, or a support having the absorbent carrier fixed thereto. A modified reagent strip including a porous matrix bearing the indicator and having exposed opposite faces, is illustrated by U.S. Pat. No. 5,187,100. A blood sample is placed in an aperture that exposes a face of the matrix, and the blood seeps from capillary effect to the opposite face. In a similar strip, the matrix is disposed between support members provided with apertures generally in line with each other.

Also known as exemplified by U.S. Pat. No. 4,092,115 to Rupe, earlier mentioned, is a test strip including a wick member enclosed in a fluid impervious sheath, and including an aperture exposing a portion of the wick member bearing colorimetric indicator. A drawback of this type of device is non-uniform color development. Also, as shown by U.S. Pat. No. 3,510,263, the faces of a chromatographic test strip may be coated with a water repellent material, and the edges may be uncoated.

Areas of use for colorimetric test strips include tap water quality testing, industrial and environmental testing, pool and spa testing, lake and stream testing, aquarium testing and other types of water testing. There continues to be a need for a colorimetric test strip of enhanced sensitivity for determination of free chlorine. It is essential that a test strip have the necessary detection capability. Stability of the indicator, uniform color development and stability of the developed color would be advantageous. Moreover, a broad range of sensitivity would be beneficial. It would be also advantageous for the test strip to be economical to manufacture.

SUMMARY OF THE INVENTION

In accordance with the present invention, a colorimetric test strip useful for and method for the analysis of free chlorine, and a process for making the test strip are provided. The test strip includes a carrier bearing a certain tetraalkylbenzidine as a colorimetric indicator. Beneficially, the carrier has been treated to have a pH that eliminates chloramine interference, and to this end, includes a buffer. Advantageously, the indicator is in the free base form. Beneficially, the carrier is a rayon, in particular, a fluid-permeable rayon; and colorimetric test additives include a nonionic fatty alcohol surfactant and a stabilizing agent.

In a preferred embodiment, the carrier may be provided with the desired pH by treatment with a combined solution of an organic liquid containing the indicator, and a water-containing solution including the buffer and effective to provide the combined solution with a pH in the range of about 6.5 to 12, preferably about 7–8. The term "solution" for purposes of this description, includes a true solution, a turbid solution and a suspension. In another preferred embodiment, the carrier may be provided with the desired pH by sequential treatment first, with the organic solution and secondly, with an aqueous solution including the buffer.

The carrier is beneficially attached to a support advantageously provided with an aperture exposing a face of the carrier. Beneficially, the opposite face of the carrier is exposed or uncovered, permitting fluid flow through the aperture and carrier.

During an analysis, the carrier may be contacted with a liquid to be analyzed, and the liquid caused to flow through the carrier and to contact the colorimetric indicator over a selected period of time. When the carrier is dipped into the liquid, a gentle swirling action is beneficially used to cause the liquid to be in flowing contact with the indicator. After the selected contact time, the carrier is evaluated for detectable color change advantageously by viewing the area of the carrier defined by the aperture.

The color may be compared to a color chart to determine the free available chlorine concentration. The color intensity that develops, increases as the concentration of the free chlorine in the sample increases and can be quantitatively determined with reproducible sensitivity and accuracy.

In the drawing and in detailed description of the invention that follows, there is essentially shown and described only a preferred embodiment of the test strip of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

DETAILED DESCRIPTION OF THE INVENTION

Figure 1:
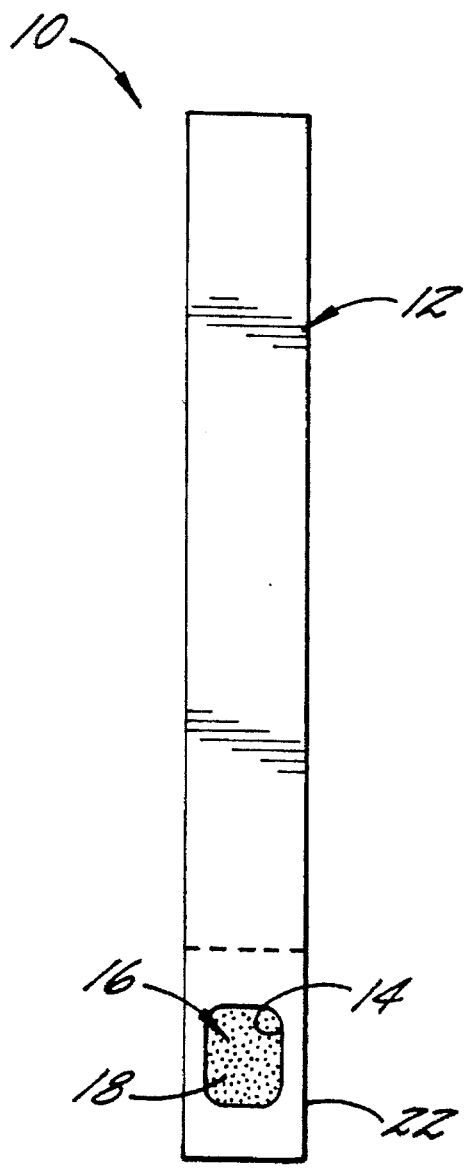
FIG. 1 is a perspective view of a test strip in accordance with the present invention.
Figure 2:
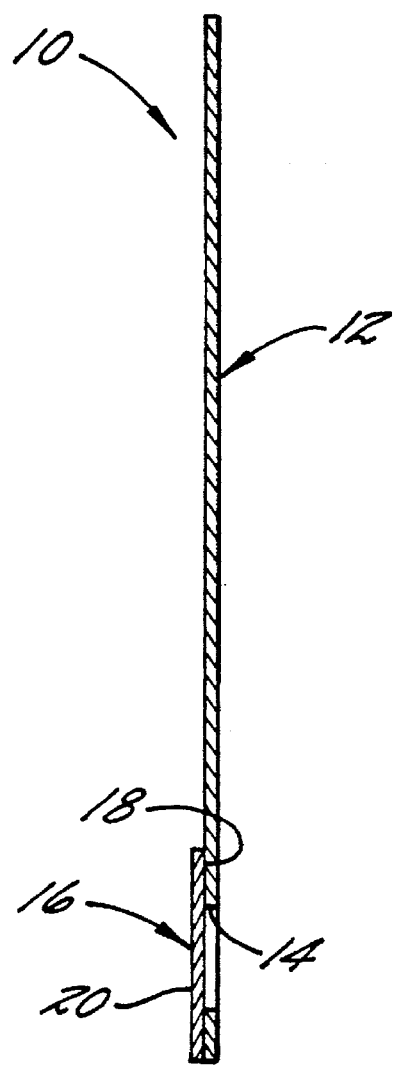
FIG. 2 is a longitudinal sectional view of the test strip of FIG. 1.

The present invention is beneficially useful for analysis of a water-based sample containing as little as 0.05 ppm (0.05 mg/L) free available chlorine, and thus provides improved sensitivity. Benefits further include stability of the indicator, visually uniform color development, and a stable colored reaction product. Advantageously, a broad concentration range may be measured by varying the sample contact time.

Referring to the drawing, a colorimetric test strip or reagent strip 10 in accordance with the present invention, is shown. Strip 10 conveniently includes a support or handle member 12, which is typically a rigid plastic strip or stick. A conventional thickness of the support ranges from about 0.008 to 0.020 inches; however, as will be understood, the thickness may vary from this range. It will be understood that the term "strip" as used herein, is not limited to an elongated strip-like shape, for the reason that such a shape is immaterial to the invention.

Various thermoplastic materials may be used as the support, with preferred materials for economy being available at low cost, for instance, recycled resins. Suitably, the support may be made of, for example, PVC or polyester. It is generally preferable that the support is white, but as can be readily appreciated, the support may be colored by, for instance, treatment with a dye.

Beneficially, at or near an end 22 of the support, an aperture 14 is provided. The aperture may have a variety of shapes such as oval, round, square, rectangular, star, triangular and diamond. Advantageously, the aperture is limited in size so as to direct fluid flow through a limited area. Typically, the aperture, when round, will be about ⅛" to ½" in diameter.

Attached to the support and located so as to be exposed by the aperture, is a carrier 16, which is advantageously fluid permeable. Fluid-permeability of the carrier and exposure of the carrier beneficially provide for fluid flow through the aperture and the carrier. The carrier will typically have a thickness of about 0.002 to 0.02 inch, with a thickness of about 0.01 inch generally being particularly suitable. It will be, of course, understood that the test strip could lack the aperture and include a conventional absorptive carrier.

Conveniently, a face 18 of the carrier may be in direct contact with the support. To enable fluid flow through the carrier, a face 20 of the carrier advantageously directly opposite to the exposed portion (as defined by aperture 14) of face 18, is beneficially exposed or uncovered. Suitably, the edges (not shown) of the carrier may also be exposed or uncovered. For purposes of this description, by "face" is meant a principal or wide surface of the carrier, as opposed to a narrow surface or edge of the carrier such as the edge of U.S. Pat. No. 3,510,263.

As may be readily appreciated, a suitable carrier maintains its structural integrity during use. Materials useful as carriers are known and include polyamide and nitrocellulose filtration materials. A rayon carrier assists in the retention of the deposited colorimetric test chemicals and in low level sensitivity, and in this regard, a filtration material commercially available as Scheicher and Schuell 8-S filter paper, is particularly useful. It will be understood that other matrices that maintain structural integrity in use, may be useful.

Deposited on the carrier is the colorimetric indicator (represented in FIG. 1 as dots). In the case of a water sample, it is generally beneficial for the indicator and other colorimetric test additives to be insoluble in or not readily soluble in water, to prevent leaching from the carrier especially during an extended sample contact time.

In accordance with the invention, the colorimetric indicator is a 3,3',5,5'-tetraalkylbenzidine, wherein alkyl is C1–C3 alkyl, in particular methyl and ethyl: 3,3',5,5'-tetramethylbenzidine (TMB) is particularly preferred. Other benzidines within the foregoing formula, include 3,3'-dimethyl, 5,5'-diethyl benzidine and 3,3',5,5'-tetraethylbenzidine. As may be understood, the four alkyl groups may be the same or different. To prevent leaching from the carrier in a water based-sample, the free base form is typically preferred.

pH treatment of the carrier and deposition of colorimetric test additives may be most desirably, for economical reasons, accomplished in a single step; however, a multi-step procedure may be useful, particularly where incompatibility or interference would result from the use of one solution. In a single step procedure involving more than one solution, solutions are combined and the carrier is treated with the combined solution. In a multi-step procedure, solutions are not combined, and the carrier member is typically dried after contact with each solution.

Treatment of the carrier may be accomplished in any of several ways. A suitable way is to pass the carrier through an impregnation bath so that the carrier becomes saturated with the impregnation solution. The carrier may then be dried at room temperature or at an elevated temperature such as about 120° to 180° F. Multiple impregnation baths would be used for multi-step procedures. However, any technique may be used that provides for the pH treatment and deposits the appropriate colorimetric test chemicals. If beneficial, the carrier may be multi-phasic.

Advantageously, the concentration of the colorimetric indicator in an impregnation solution and the residence time of the carrier in the solution are selected to ensure deposition of the appropriate amount of the indicator. Generally speaking, the residence time is usually not significant, and may vary from several seconds to several minutes, typically about two to ten seconds, depending upon the carrier. Typically, from about 0.05 to 2 mg, preferably about 1 to 1.5 mg, of colorimetric indicator will be deposited per test strip, for a strip of about 0.011" thickness, ⅜" width and ½" height, but in any case, the amount deposited will be sufficient for colorimetric determination of free chlorine. In the case of the tetraalkylbenzidines, it has been found that stable color development is suitably provided for, by using a solution level of about 0.5 wt. %.

Advantageously, the solution containing the indicator, may include a wetting agent for improved wetting of the carrier and other beneficial effects including enhancement of color development. Beneficially, the wetting agent is substantially insoluble in the liquid to be analyzed, to prevent leaching from the carrier. Especially useful is a nonionic surfactant, in particular a polyethoxylated fatty alcohol, nonionic surfactant commercially available from GAF under the name Emulphor ON870. By comparison, without this surfactant, color intensity may be reduced by about ⅓ to ½. Other suitable wetting agents, with suitability typically depending upon the carrier selected, include an anionic surfactant such as dioctyl sodium sulfosuccinate. Generally speaking, the indicator solution may include about 2 to 4:1, especially suitably about 3:1, of the tetraalkylbenzidine to wetting agent, on a weight basis.

In addition, the solution containing the indicator, may beneficially include a stabilizing agent for preventing undesired degradation of the indicator. Beneficially, this agent is likewise substantially insoluble in the liquid to be analyzed, to prevent leaching from the carrier. Illustrative is an interpolymer of a lower alkylvinyl ether, and a lower alkyl-substituted or unsubstituted, 1,2-ethylenedicarboxylic acid lower alkyl monoester. By "lower alkyl" is meant methyl, ethyl and propyl. Suitably, the interpolymer is an equimolar reaction product. Particularly useful is an interpolymer of methylvinyl ether and maleic acid isopropyl monoester, which is commercially available from GAF Corporation as Gantrez ES-335 I. Incorporated herein by reference is disclosure relating to the related anhydride and set forth in U.S. Pat. No. 3,453,180. Generally speaking, the indicator solution may advantageously include about 6 to 8:1, particularly suitably about 7:1, of the stabilizer to the indicator, on a weight basis.

In accordance with the invention, the carrier is beneficially treated with an organic or inorganic buffer for providing the appropriate pH. In accordance with the invention, it has been found that pH is an important factor in preventing chloramine interference when determining free chlorine. Exemplary buffers include phosphate buffers such as monosodium phosphate (MSP), disodium phosphate (DSP) and trisodium phosphate (TSP), and organic buffers such as N-[2-hydroxyethyl]piperazine-N'-[2-hydroxypropane-sulfonic acid] known as HEPPSO, 3-[N-tris(hydroxymethyl)methylamino], 2-hydroxypropanesulfonic acid] known as TAPS, and N,N-bis[2-hydroxyethyl]glycine known as BICINE. An acid buffer such as MSP, may be used provided that the pH can be adjusted to be within the appropriate range, using for instance, a caustic such as sodium hydroxide.

Regardless whether a single step procedure or multi-step procedure is used for pH treatment of the carrier and colorimetric chemical deposition, multiple solutions are usually prepared, with one solution including an organic liquid for solubilizing the free base form of the tetraalkyl-benzidine, and another solution including water for solubilizing a water-soluble buffer. Suitable organic liquids for a multi-step procedure include acetone, ethanol, toluene and so forth. However, in the case of a single step procedure and a water-soluble buffer, the organic liquid must be selected to maintain solubility or dispersion of the buffer adequate for the necessary pH treatment of the carrier. To this end, an ethanol/acetone solvent has been found useful, with a suitable ratio ranging from about 6 to 4:1, preferably about 5:1, of ethanol to acetone, on a weight basis. Advantageously, reagent grade ethanol and purified acetone are used. Beneficially, the ethanol/acetone solvent may provide sufficient stability when combined with an aqueous solution, for the combined solution to be useful for an hour or more. As can be understood, it has been found to be beneficial to use the organic liquid to solubilize the surfactant, stabilizer and indicator.

Beneficially, in accordance with the invention, the carrier is treated to have a pH effective to prevent chloramine interference. It has been found that a carrier pH of at least about 5.75 is typically effective for preventing chloramine interference; however, generally speaking, a preferred lower pH limit is about 6.0 to 6.2. The upper pH is limited by factors including stability, and in this regard, although a carrier pH of about 10 may be operative, it is, generally speaking, preferred for the pH to have an upper limit of about 7.

Treatment of the carrier to provide an appropriate pH may be advantageously accomplished in a single dip procedure. In this case, the dip solution should have a pH of at least about 6.5 and of no more than about 12. Preferably, the pH of the dip solution is in the range of about 7 to 8. In using a single dip procedure, stability of the dip solution may be enhanced by use of an organic buffer, rather than an inorganic buffer.

In the case of a two dip procedure, when the organic solution has a pH of about 5.4, a useful pH range for the buffer solution may be from about 7 to 12, preferably about 8.7 to 12. In addition, prevention of chloramine interference may require dipping in the indicator solution prior to the buffer solution for certain buffers. Illustrative are organic buffers that may be leached from the carrier by an organic liquid-containing solution of the indicator. This criticality may be due to leaching or other undesired adjustment of the carrier pH when the carrier is being dipped in the organic liquid. Exemplary organic buffers are HEPPSO and TAPS. As indicated, it is necessary that the pH of the treated carrier prevent chloramine interference, regardless whether a single step dip or multi-step dip is used.

It may be beneficial to deposit on the carrier an additive for fixing the indicator on the carrier. Illustrative is a polymeric film former such as polyvinyl pyrrolidone. Exemplary is polyvinyl pyrrolidone having an average molecular weight of 60,000 and commercially available as PVP K-60 Solution (PVP-60).

If desired, one or more coagents or agents otherwise assisting in the analysis, may also be deposited onto and/or within the carrier. However, for free chlorine analysis, it is not contemplated that a copper salt, peroxide, oxidase or other enzymatic coagent will be used. As a result, the carrier will be free of a cupric salt, peroxide, oxidase or other enzymatic coagent.

Attachment of the carrier to the support may be accomplished in a variety of ways. A suitable way is by use of a double-faced adhesive material. The adhesive material is layered down onto the support with tape liner on top. The aperture may then be punched out, the tape liner removed, and the carrier affixed by the adhesive surrounding the aperture. Other suitable methods for attaching the carrier to the support include heat sealing and ultrasonic sealing. Still another method is to dispose the carrier between two supports provided with apertures generally in line with each other. It will be understood that the method of attachment is not limited to the methods just described.

Advantageously, the time of contact of the liquid being tested, with the indicator, is selected to ensure the appropriate sensitivity. Typically, the time will vary from about 1 second to 90 seconds for free chlorine.

Typically, without adjustment of the unknown sample pH, the carrier is dipped into the liquid to be analyzed. When a dip-and-read technique is sufficient for the sensitivity needed, the carrier is immediately withdrawn. However, when enhanced contact is desirable, a gentle swirling action is beneficially used to cause the liquid to be in flowing contact with the indicator, after which the carrier is withdrawn from the liquid. A vigorous action as employed is U.S. Pat. No. 4,904,605, is typically unnecessary and may even be detrimental. Accordingly, by the term "gentle action" is meant mild or moderate action. The test strip may be moved within the liquid in a variety of ways, for instance, back and forth, or using rotational motion. In any event, whether the action is gentle or vigorous, and regardless of the type of motion used, uniformity of color development will be found within the area defined by the aperture.

It is, of course, not necessary to immerse the carrier in the liquid; for instance, the carrier may be contacted with flowing tap water. Regardless whether the carrier is dipped or not, an extended contact time for purposes of this invention, is about five seconds or more, with about ten seconds or more frequently being desirable, and with about forty seconds or more, even ninety seconds, being highly useful in certain instances.

After the selected contact time, the carrier is evaluated for detectable color change. Beneficially, with respect to the embodiment of the drawing, color is evaluated from the aperture side of strip 10. By comparison, the color on opposite face 20 may be non-uniform outside the area defined by aperture 14. When the carrier is disposed between supports provided with apertures generally in line with each other, the color may be evaluated by viewing the color within either aperture.

The following examples illustrate the analysis of free available chlorine in water-based samples. In these examples and throughout this description, all parts and percentages are weight percent unless otherwise specified.

Example 1

Solutions A and B are prepared, and while stirring solution A (pH 5.4), solution B (pH 8.7) is added slowly thereto. The combined solution has a pH of about 7.

| Solution A | |
|---|---|
| Tetramethylbenzidine | 0.6 g |
| Acetone (purified) | 10.0 g |
| Ethanol (absolute) | 50.0 g |
| Gantrez ES-335 I | 4.0 g |
| 10% Emulphor ON870 in Ethanol | 2.0 g |
| Solution B | |
| Water | 60.0 g |
| Disodium phosphate | 1.0 g |

Rayon filter paper commercially available as Scheicher and Schuell 8-S filter paper, is dipped into the combined solution for several seconds and dried. The solution is stable for one hour or more. The impregnated, dried filter paper is disposed over a ¼" diameter aperture in a rigid, white polyester support and attached to the support by heat sealing. The support is 0.008" thick, ⅜" wide and 2½" long. Based upon an accelerated stability study at an elevated temperature of 55° C., the resulting test strip is expected to have at least 2 years stability at room temperatures when stored with a desiccant.

Chlorine standards from sodium hypochlorite are prepared with levels of 0.05, 0.1, 0.2, 0.5, 1.0, 2.0, 5.0, 10.0, and 25 ppm. The chlorine levels are confirmed using a reference analytical test method.

Dip times of 1, 10, 30 and 90 seconds are used during which time (except for the 1 second dip) the strips are constantly and gently swirled in the chlorine standards to effect liquid flow through the filter paper carrier. After the selected dip time, the strip is removed from contact with the liquid and visually inspected for color change.

Color uniformity on the filter paper is observed in the area defined by the aperture. The color is observed to be stable for several minutes, the only color change being due to drying of the filter paper. The relationship of free chlorine level and dip time to the color developed, is shown in Table 1.

As indicated in Table 1, low level sensitivity is enhanced as dip time is increased. Thus, sensitivity of free chlorine levels less than 1 ppm is realized using a dip time of about 5 to 10 seconds or more, with sensitivity of even about 0.05 ppm being obtained using a dip time of about 90 seconds. Compared to conventional chlorine test strips having a sensitivity of about 1 ppm, an about 20-fold improvement is provided. While not in any way being bound by this theory, it seems that the aperture functions to direct fluid flow through a limited area and thereby provides enhanced contact of colorimetric reagent with free chlorine. Also shown in Table 1 is a broad detection range of 0.05 to 25 ppm free chlorine, with visually distinctive color development at intermediate levels, using more than one dip time.

In swimming pools, a free chlorine level of about 1 ppm is typically considered to be ideal, with a range of about 0.4 to 2 ppm being usually acceptable. A dip time of about ten seconds beneficially distinguishes levels ranging from about 0.2 to 3 ppm. When superchlorinating, the target free chlorine level is approximately 8 to 10 ppm. A dip time of about 1 second would be advantageously used to check the level after superchlorinating.

In tap water, a free chlorine level of about 0.2 ppm is generally considered to be normal. Therefore, as

TABLE 1

| Free Chlorine level PPM | Color found after dip time (in seconds) | | | |
|---|---|---|---|---|
| | 1 | 10 | 30 | 90 |
| 0 | White | White | White | White |
| 0.05 | White | White | White | Very Lt Blue |
| 0.1 | White | White | Very Lt Blue | very lt Blue |
| 0.2 | White | Very Lt Blue | Very Lt Blue | Lt Blue |
| 0.5 | White | Lt Blue | Lt Blue | Blue |
| 1.0 | Very Lt Blue | Blue | Blue | Dk Blue |
| 2.0 | Lt Blue | Dk Blue | Very DK Blue | Very Dk Blue |
| 5.0 | Blue | Very Dk Blue | Very Dk Blue | Very Dk Blue |
| 10 | Dk Blue | Very Dk Blue | Very Dk Blue | Very Dk Blue |
| 25 | Very Dk Blue | Very Dk Blue | Very Dk Blue | Very Dk Blue | shown in Table 1, a dip time of about 30 seconds beneficially provides the needed sensitivity. Accordingly, the dip time selected, depends upon the free chlorine level of interest.

Example 2

Solutions are prepared in accordance with the formulations of solutions A and B in Example 1, except that the same weight percent of tribasic sodium phosphate is substituted for the dibasic phosphate. The two solutions are combined as in Example 1, and the combined solution is found to have a pH of about 7.8. The filter paper is dipped into the combined solution and thereafter dried. The resulting test strip is found to be effective in determining free chlorine. No chloramine interference is found.

Also tested and found to be effective in determining free chlorine, were test strips prepared by impregnation with combined solutions in which HEPPSO, TAPS and BICINE were substituted for the dibasic phosphate. In each case, the pH of the buffer solution was appropriately adjusted with caustic prior to combining the organic solution and the aqueous buffer solution.

Example 3

Solutions are prepared in accordance with the formulations of solutions A and B in Example 1, except that the same weight percent of monobasic sodium phosphate is substituted for the dibasic phosphate. The pH of the buffer solution is adjusted using sodium hydroxide. The two solutions are combined as in Example 1. The combined solution has a pH of 5.25, as shown in Table 2 (Run 1, Soln pH). Solution pH is determined by pH meter.

The filter paper is dipped into the combined solution and thereafter dried. The dried, treated paper is

TABLE 2

| Run | Soln pH | Carrier pH | Free chlorine | Chloramine interf |
|---|---|---|---|---|
| 1 | 5.25 | 6.03 | yes | yes |
| 2 | 5.75 | 5.61 | yes | yes |
| 3 | 6.0 | 5.56 | yes | yes |
| 4 | 6.3 | 5.73 | yes | yes |
| 5 | 6.6 | 5.75 | yes | no |
| 6 | 7.0 | 6.20 | yes | no |
| 7 | 7.3 | 6.38 | yes | no |
| 8 | 7.9 | 6.94 | yes | no |
| 9 | 8.8 | 7.67 | yes | no |
| 10 | 10.6 | 8.09 | yes | no |
| 11 | 12 | 10.04 | yes | no |

TABLE 3

| Run | Buffer | Buffer Soln pH | B/A | A/B |
|---|---|---|---|---|
| 1 | MSP | 8.72 | yes | yes |
| 2 | DSP | 11.83 | yes | yes |
| 3 | HEPPSO | 8.76 | no | yes |
| 4 | TAPS | 8.74 | no | yes | found to have a pH of 6.03, as shown in Table 2 (Run 1, Carrier pH). The carrier pH is determined as now explained. The face of a flat surface electrode is covered with the dried, treated paper. 1 or 2 drops of distilled water are used to wet the paper. Good contact is ensured between the face of the electrode and the paper. The pH reading is allowed to stabilize, and thereafter the reading is taken.

The effectiveness of the test strip for determining free chlorine is tested. Chloramine interference is evaluated. The result is shown in Table 2.

The foregoing procedure is repeated, with the pH being varied as shown in Runs 2–11 of Table 2. The pH of the combined solution is determined in each case. The pH of the dried, treated carrier is determined in each case. The effectiveness of each test strip for determining free chlorine is tested. Chloramine interference is evaluated. The results of Runs 2–11 are shown in Table 2.

As can be understood from Table 2, chloramine interference is present using a combined solution having a pH of 6.3, but is eliminated when the combined solution has a pH of 6.6 or more.

The free chlorine test requires that chloramine levels typically found in water such as below 4 ppm, will not cause any color development with the free chlorine test. In evaluating for chloramine interference, reaction levels of chloramine at a concentration of 10 ppm, must not yield free chlorine color development above about 0.3 ppm.

Example 4

With reference to Run 2 of Table 3, solutions are prepared in accordance with the formulations of solutions A and B in Example 1. With reference to Runs 1, 3 and 4 of Table 3, solutions are prepared in accordance with the formulations of solutions A and B in Example 1, except that the same weight percent of the buffer shown in Table 3 is substituted for the dibasic phosphate.

In each case, the pH of the buffer solution is adjusted to the pH shown, using sodium hydroxide. In each case, the two solutions are not combined, and the filter paper is dipped into the two solutions and dried between dips. With reference to Table 3, "A/B" means dipped first in Solution A, and "B/A" means dipped first in Solution B.

The effectiveness of resulting test strip is tested, and the result is shown in Table 3. With reference to the Table, "yes" means effective for free chlorine, no chloramine interference, and "no" means chloramine interference.

Comparative Example

The following solution is prepared, and Scheicher and Schuell 8-S filter paper is dipped into the solution for several seconds and thereafter dried.

| | |
|---|---|
| syringaldazine | 0.1 g |
| vanillinazine | 0.1 g |
| ethanol | 75.0 g |
| phosphate buffer (0.1M) | 15.0 g |

The impregnated, dried filter paper is disposed over a ¼", star-shaped aperture in a rigid, white PVC support and attached to the support by ultrasonic sealing. The support is 0.008" thick, ⅜" wide and 3" long.

Free chlorine standards are prepared with levels of 0.2, 0.5, 1.0, 2.0, 5.0 and 10 ppm. The chlorine levels are confirmed using a reference analytical test method.

Dip times of 1, 10, 30 and 60 seconds are used during which time (except for the 1 second dip) the strips

TABLE 4

| Free Chlorine | Color Found After Dip Times (in seconds) | | | |
|---|---|---|---|---|
| PPM | 1 | 10 | 30 | 60 |
| 0 | White | White | White | White |
| 0.2 | White | White | White | V. Lt. Lavender |
| 0.5 | White | White | V. Lt Lav. | Lt. Lavender |
| 1.0 | V. Lt. Lav. | V. Lt Lav. | Lt. Lav. | Lavender |
| 2.0 | Lt. Lavender | Lt. Lav. | Dk. Lav. | Purple |
| 5.0 | Lavender | Lavender | Dk. Lav. | Dk. Purple |
| 10.0 | Purple | Purple | Purple | Dk. Purple | are constantly and gently swirled in the chlorine standards to effect liquid flow through the filter paper carrier. After the selected dip time, the strip is removed from contact with the liquid and visually inspected for color change.

Uniformity of color on the carrier is observed in the area defined by the aperture. However, the color is observed to fade and therefore color match must be done immediately. The relationship of chlorine level and dip time to the color developed, is shown in Table 4. Comparison with the results in Table 1 reveals greater sensitivity by advantageously using a colorimetric test composition including a tetraalkylbenzidine in accordance with the invention.

The present invention may be carried out with various modifications without departing from the spirit or essential attributes thereof, and accordingly, reference should be made to the appended claims, rather than to the foregoing specification as indicating the scope of the invention.

What is claimed is:

1. A colorimetric test strip useful for analysis of free chlorine, said test strip comprising a carrier bearing 3,3',5,5'-tetraalkylbenzidine having C1–C3 alkyl groups, wherein said alkyl groups may be the same or different, said carrier having been treated to have a pH effective to prevent chloramine interference.

2. The test strip of claim 1, wherein said pH of said carrier is in the range of about 5.75 to 10.

3. The test strip of claim 2, said carrier having been treated with a combined solution formed from an organic liquid-containing solution of said tetraalkylbenzidine, and a water-containing solution comprising a buffer and effective to provide said combined solution with a pH in the range of about 6.5 to 12.

4. The test strip of claim 2, said carrier having been sequentially treated with first, an organic liquid-containing solution of said tetraalkylbenzidine, and secondly, a water-containing solution of said buffer, said carrier being dried between said sequential treatments.

5. The test strip of claim 1, wherein said pH of said carrier is in the range of about 6 to 7.

6. The test strip of claim 1, wherein said tetraalkylbenzidine is in the free base form.

7. The test strip of claim 1, wherein said tetraalkylbenzidine is 3,3',5,5'-tetramethylbenzidine, and said pH of said carrier is in the range of about 6 to 7.

8. The test strip of claim 1, wherein said carrier is made of rayon and includes a polyethoxylated fatty alcohol, nonionic surfactant.

9. The test strip of claim 1, wherein said carrier includes a stabilizing agent.

10. The test strip of claim 7, wherein said stabilizing agent is an interpolymer of a lower alkylvinyl ether and a 1,2-ethylenedicarboxylic acid lower alkyl monoester, the ethylene moiety having substituents selected from hydrogen and lower alkyl groups, said lower alkyl being C1–C3 alkyl.

11. The test strip of claim 1, wherein said carrier is made of rayon.

12. A method for analysis of free chlorine, said method comprising contacting an unknown sample with the test strip of claim 1, wherein said pH of said carrier is in the range of about 6 to 7, and said tetraalkylbenzidine is 3,3',5,5'-tetramethylbenzidine.

13. The test strip of claim 1, wherein said pH of said carrier is in the range of about 6.2 to 7.

14. A method for analysis of free chlorine, said method comprising contacting an unknown sample with a test strip comprising a carrier treated with a combined solution of an organic liquid-containing solution of 3,3',5,5'-tetraalkylbenzidine having C1–C3 alkyl groups, wherein said alkyl groups may be the same or different, and a water-containing solution comprising a buffer and effective to provide the treated carrier with a pH effective to prevent chloramine interference; and evaluating the coloration on said carrier.

15. The method of claim 14, wherein said tetraalkylbenzidine is in the free base form.

16. The method of claim 14, wherein said tetraalkylbenzidine is 3,3',5,5'-tetramethylbenzidine, wherein said pH of said carrier is in the range of about 6 to 7, and wherein said carrier is made of rayon and includes a polyethoxylated fatty alcohol, nonionic surfactant.

17. A process for making a colorimetric test strip useful for analysis of free chlorine, said process comprising treating a carrier with a combined solution of an organic liquid-containing solution of 3,3',5,5'-tetraalkylbenzidine having C1–C3 alkyl groups, wherein said alkyl groups may be the same or different, and a water-containing solution comprising a buffer and effective to provide the treated carrier with a pH effective to prevent chloramine interference, and drying said carrier after said impregnation.

18. The process of claim 17, wherein said water-containing solution is effective to provide said carrier with a pH in the range of about 6 to 7.

19. The process of claim 17, wherein said tetraalkylbenzidine is in the free base form.

20. The process of claim 17, wherein said organic liquid-containing solution comprises a nonionic surfactant and a stabilizing agent.

* * * * *